United States Patent
Carre

(10) Patent No.: US 6,461,734 B1
(45) Date of Patent: Oct. 8, 2002

(54) SUBSTRATE FOR ARRAY PRINTING

(75) Inventor: Alain R. E. Carre, Le Chatelet-en-Brie (FR)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 09/245,142

(22) Filed: Feb. 4, 1999

Related U.S. Application Data

(60) Provisional application No. 60/076,311, filed on Feb. 27, 1998.

(30) Foreign Application Priority Data

Feb. 4, 1998 (EP) ............................................. 98400242

(51) Int. Cl.⁷ ................................................. B32B 9/00
(52) U.S. Cl. ........................ 428/429; 428/426; 428/446; 428/447; 428/141; 501/66
(58) Field of Search ................................ 428/156, 429, 428/426, 446, 447, 704, 410, 141; 501/66

(56) References Cited

U.S. PATENT DOCUMENTS

| | | | |
|---|---|---|---|
| 3,819,972 A | * | 6/1974 | Sanner |
| 4,407,966 A | * | 10/1983 | Kerko et al. |
| 4,994,373 A | * | 2/1991 | Stavrianopoulos et al. |
| 5,374,595 A | | 12/1994 | Dumbaugh, Jr. et al. |
| 5,474,796 A | | 12/1995 | Brennan |
| 5,510,270 A | * | 4/1996 | Fodor et al. |
| 5,840,256 A | * | 11/1998 | Demers et al. |
| 5,863,708 A | * | 1/1999 | Zanzucchi et al. |
| 6,248,521 B1 | * | 6/2001 | Van Ness et al. |

FOREIGN PATENT DOCUMENTS

| | | |
|---|---|---|
| EP | 0 035 719 A2 | 9/1981 |
| WO | WO 93/09668 | 5/1993 |

OTHER PUBLICATIONS

L. J. Urbanek, "Functionalized Inorganic Surface Materials Modified by Chemically Bound (1–phenylethyl)Aminopropyl Groups and Their Preparation", Chemical Abstracts, vol. III, No. 20, Nov. 13, 1989, Abstract No. 177392, p. 201.

* cited by examiner

Primary Examiner—Deborah Jones
Assistant Examiner—Jennifer McNeil
(74) Attorney, Agent, or Firm—Thomas R. Beall; Vincent T. Kung

(57) ABSTRACT

A substrate for use in supporting high density biological or chemical arrays that is made from borosilicate or boroaluminosilicate glass. It has been demonstrated that a functionalized coating used to immobilize oligonucleotides for example, retains its functionality when exposed to environmental stresses when it is applied to a slide composed of a glass material having a low sodium oxide content.

23 Claims, No Drawings

SUBSTRATE FOR ARRAY PRINTING

RELATED APPLICATIONS

This application claims the benefit of European Application No. 98400242.8, filed Feb. 4, 1998 and U.S. Provisional Application No. 60/076,311, filed Feb. 27, 1998.

FIELD OF INVENTION

The invention relates to high density biological and chemical arrays and specifically to an improved substrate material onto which arrays are deposited.

BACKGROUND OF INVENTION

Oligonucleotide hybridization is widely used to determine the presence in a nucleic acid of a sequence that is complimentary to the oligonucleotide probe. In many cases, this provides a simple, fast, and inexpensive alternative to conventional sequencing methods. Hybridization does not require nucleic acid cloning and purification, carrying out base-specific reactions, or tedious electrophoretic separations. Hybridization of oligonucleotide probes has been successfully used for various purposes, such as analysis of genetic polymorphisms, diagnosis of genetic diseases, cancer diagnostics, detection of viral and microbial pathogens, screening of clones, genome mapping and ordering of fragment libraries.

An oligonucleotide array is comprised of a number of individual oligonucleotide species tethered to the surface of a solid support in a regular pattern, each one in a different area, so that the location of each oligonucleotide is known. An array can contain a chosen collection of oligonucleotides, e.g., probes specific for all known clinically important pathogens or specifics for all known sequence markers of genetic diseases. Such an array can satisfy the needs of a diagnostic laboratory. Alternatively, an array can contain all possible oligonucleotides of a given length n. Hybridization of a nucleic acid with such a comprehensive array results in a list of all its constituent n-mers, which can be used for unambiguous gene identification (e.g., in forensic studies), for determination of unknown gene variants and mutations (including the sequencing of related genomes once the sequence of one of them is known), for overlapping clones, and for checking sequences determined by conventional methods. Finally, surveying the n-mers by hybridization to a comprehensive array can provide sufficient information to determine the sequence of a totally unknown nucleic acid.

Oligonucleotide arrays can be prepared by synthesizing all the oligonucleotides, in parallel, directly on the support, employing the methods of solid-phase chemical synthesis in combination with site-directing masks as described in U.S Pat. No. 5,510,270. Using an efficient photolithographic technique, miniature arrays containing as many as $10^5$ individual oligonucleotides per $cm^2$ of area have been demonstrated.

Another technique for creating oligonucleotide arrays involves precise drop deposition using a piezoelectric pump as described in U.S Pat. No. 5,474,796. The piezoelectric pump delivers minute volumes of liquid to a substrate surface. The pump design is very similar to the pumps used in ink jet printing. This picopump is capable of delivering 50 micron and 65 picoliter droplets at up to 3000 Hz and can accurately hit a 250 micron target. When energized, a microdroplet is ejected from the pump and deposited on the array plate at a functionalized binding site.

Further approaches to forming an array involve repeatedly contacting a substrate surface with typographic pins holding droplets and using ink jet printing mechanisms to lay down an array matrix.

In choosing a substrate for use as a support for the attachment of oligonucleotides, several characteristics must be considered. First, the surface must be compatible with the method of detection of hybridization. Spectroscopic, chemiluminescent and fluorescent detection techniques are the detection techniques of choice for DNA research involving high density arrays. In order to use these techniques, it is desirable that the substrate be optically transparent. A second important characteristic is that the linkage of the penultimate oligonucleotide to the surface have high chemical stability, at least equal to that of the polyphosphate backbone in DNA.

The substrates that support the arrays are conventionally 1 by 3 inch slides made from soda lime glass and coated with a polar silane, which contains for example an amino group suitable for anchoring solid phase oligonucleotide synthesis, and specifically for cross-linking DNA molecules. Photoresist or masking techniques may be used to make patterned derivitization on such a surface. In this way, one can achieve patterned wetting sites on an otherwise nonwetting surface, as well as patterned functionalized sites on an otherwise nonfunctionalized surface.

One problem with the conventional use of soda lime glass as a substrate for the support of high density arrays is the presence of particulate contamination that is common in the production of such low grade glass. Particulate contamination is of special concern while dealing with samples on such small scale as 10,000 target sites per slide. Further, the sodium contained in soda lime glass can be easily mobilized to exit the glass. Hazing is a result which negatively affects the transparency of the glass and consequently disturbs the detection techniques previously mentioned. Finally, it is difficult to obtain a uniform functionalized coating, such as an amino functional silane coating, on the surface of the slides now in conventional use. Without a uniform coating, oligonucleotide attachment is uneven, leading to varied and unreliable detection results.

SUMMARY OF INVENTION

An improved substrate for use in the printing or the synthesis of biological and chemical arrays is disclosed. The substrate is a substantially flat support made from a borosilicate or boroaluminosilicate glass.

DETAILED DESCRIPTION OF THE INVENTION

The functionalized coating of the surface of glass substrates with amino functionalized amines, for example, is the backbone of high density array manufacture. A substantially even coating of the functionalized coating, as discussed above, is required. It has been discovered that using a known glass that can be manufactured by known methods to obtain a specific smoothness has important uses as a biological substrate.

The substrate of the present invention, which preferably takes the form of a 1 inch×3 inch slide, is made from a borosilicate or boroaluminosilicate glass. In one preferred embodiment, the substrate glass (1737 LCD glass available from Corning Incorporated) has a composition, in terms of mole percent, consisting essentially of:

| | | | |
|---|---|---|---|
| SiO$_2$ | 67.6 | BaO | 4.31 |
| Al$_2$O$_3$ | 11.4 | MgO | 1.31 |
| B$_2$O$_3$ | 8.53 | SrO | 1.29 |
| CaO | 5.2 | As$_2$O$_3$ | 0.39 |

In other preferred embodiments (e.g., commercially designated 7059 LCD glass from Corning Incorporated), the slide is made from several suitable boroaluminosilicate glass compositions that are listed in commonly assigned U.S. Pat. No. 5,374,595. A glass described in U.S. Pat. No. 5,374,595, has a composition, in mole percent, consisting essentially of:

| | | | |
|---|---|---|---|
| SiO$_2$ | 64–70 | Y$_2$O$_3$ | 0–5 |
| Al$_2$O$_3$ | 9.5–14 | MgO | 0–5 |
| B$_2$O$_3$ | 5–10 | CaO | 3–13 |
| TiO$_2$ | 0–5 | SrO | 0–5.5 |
| Ta$_2$O$_5$ | 0–5 | BaO | 2–7 |
| Nb$_2$O$_5$ | 0–5 | MgO + CaO + SrO + BaO | 10–20 |

Generally, the preferred glass compositions for the substrate slide will have a sodium oxide, or any other alkali metal oxide, content of less than about 15 weight percent.

The slides may be cut from a sheet of glass that has been formed by a fusion draw process as described in U.S. Pat. Nos. 3,338,696 and 3,682,609, which are both incorporated herein by reference. This disclosed process provides for the manufacture of high liquidus viscosity glasses, such as borosilicates or boroaluminosilicates, in sheets having an extremely even and smooth surface. Each slide has a uniform surface smoothness, such that the average roughness (Ra) of a major or top surface, as taken on a 20 micron by 20 micron scan employing an atomic force microscope (AFM), is less than about 10 nanometers, and preferably less than 10 angstroms. Even more preferably, the average roughness is less than 5 angstroms. As used herein, the "top surface" is the portion of the slide onto which a binding entity array is synthesized, deposited, or otherwise attached. When used to produce 1737 LCD glass, for example, the fusion draw process for forming flat glass, as disclosed in the U.S. patents cited above, provides a surface with a preferred average roughness of less than 5 angstroms. Although the borosilicate or boroaluminosilicate sheets may be manufactured by other methods and subsequently polished to the desired roughness, the fusion draw process is more preferred, since polishing steps in manufacture tends to lead to particulate contamination on the substrate surface, which can roughen or otherwise damage the surface. The smoothness of the surface helps enable the application of a uniform surface coating.

The coating that is preferably applied to the borosilicate or aluminosilicate substrate for use in oligonucleotide immobilization is a polar silane which contains for example an amino group suitable for anchoring solid phase oligonucleotide synthesis, and specifically for cross linking the DNA molecules. Alternatively, the polar silane may contain a hydroxyl after hydrolysis (before hydrolysis, this group is preferably an alkoxy group). Suitable coatings include functionalized alkoxysilane or chlorosilane whereby the silane has between 1 and 3 alkoxy or chlorine groups. Further, the top surface may have patterned derivitization through the use of photoresist or masking techniques, for example.

Use of the borosilicate or boroaluminosilicate substrate is not limited to amine functionalized coatings for oligonucleotide array support. The substrate may be used as a solid support for any of a variety of binding entities, which may include any biological or synthetic molecule having a specific affinity for another molecule, through either covalent or non-covalent binding. Preferably, a specific binding entity contains (either by nature or by modification) a functional chemical group (primary amine, sulfhydryl, aldehyde, carboxylic, acrylic, etc.), a common sequence (nucleic acids, an epitope (anitbodies), a hapten, or a ligand, that allows the binding entity to bond or react covalently or non-covalently with a common function group on the surface of a substrate. Specific binding entities include, but are not limited to: deoxyribonucleic acids (DNA), ribonucleic acids (RNA), synthetic oligonucleoides, antibodies, proteins, peptides, lectins, modified polysaccarides, synthetic composite macromolecules, functionalized nanostructures, synthetic polymers, modified/blocked nucleotides/nucelosides, modified/blocked amino acids, fluorophores, chromophores, ligands, chelates, and haptens.

EXAMPLE

A comparison study was performed to determine the durability of an identical coating applied 1"×3" slides made of three different glasses: soda-lime glass, borosilicate glass, and boroaluminosilicate glass. A coating of gamma-aminopropyl triethoxysilane was applied to each of the slides to be tested. The slides were then immersed in boiling water for a period of time ranging from 0.5 to 5 hours. When the aminated coating is retained on the surface of the slide after exposure to certain environmental stresses (in this instance, boiling water), the functionality of the surface is said to have retained its functionality and the result of the test for durability is positive.

The durability of the aminated coating was measured by using a staining test based on a Au/Ag growth process. This process reveals the presence of amine functions on the substrate surface. When Au/Ag growth occurs, the test is positive for the presence of amine functions. A positive test is indicated by visual observation of a dense and uniform metal gray coating. A substrate free of amine functionality does not stain and remains clear.

The staining process test was conducted as follows: The slides were dipped in AURODYE FORTE RPN 490 (Amersham Life Science, Amersham International) for 1 hour. The slides were then rinsed with pure water. The slides were then dried with N$_2$.

The slides were next dipped in INTENSE BL SILVER ENHANCEMENT SOLUTION RPN 492 (Amersham Life Science, Amersham International) for 5 minutes. The slides were then again rinsed with pure water and dried with N$_2$. The presence or absence of a metal gray coating was determined by visual observation.

As mentioned, substrates made of three different materials, namely soda lime glass, borosilicate glass, and boroaluminosilicate glass, were tested. Table 1 shows the length of exposure in boiling water required for the gamma-aminopropyl triethoxysilane coated slide to lose its amine functionality (time required for the staining test to read negative).

TABLE 1

| Glass Substrate | Coating Durability (in hours) |
|---|---|
| Soda-Lime Glass | 0.5 |
| Borosilicate Glass | 2.0 |

TABLE 1-continued

| Glass Substrate | Coating Durability (in hours) |
|---|---|
| Boroaluminosilicate Glass (1737 LCD Glass) | 4.0 |

The results shown in Table 1 demonstrate that the durability of the gamma-aminopropyl triethoxysilane coating on borosilicate or boroaluminosilicate glasses is far superior to that of the same coating on soda-lime glass.

Although not intending to be bound by the explanation, it is thought that the lower or nonexistent levels of sodium oxide in the samples of borosilicate and boroaluminosilicate glass provide the advantageous durability characteristics shown in the testing. Preferably, the glass material as used for the high density assay substrate has a sodium oxide content of less than 12 mole percent, and even more preferably less than 8 mole percent, and more preferably still, no sodium oxide content at all. For this reason it may be contemplated, as an alternative, to use any glass that has this requisite sodium oxide content including aluminosilicate glass, for example.

The composition of soda-lime glass is given as an example in Table 2. The composition of borosilicate glass, as used in this example, is given in Table 3. The composition of 1737 LCD glass, the boroaluminosilicate glass used in this example, is given above.

TABLE 2

| Compound | Mole Percent (%) |
|---|---|
| $SiO_2$ | 71.5 |
| $Na_2O$ | 13.3 |
| $K_2O$ | 0.3 |
| CaO | 8 |
| MgO | 4.1 |
| $Al_2O_3$ | 1.5 |
| $SO_3$ | 0.37 |
| $TiO_2$ | 0.06 |
| $Fe_2O_3$ | 0.07 |
| $As_2O_3$ | 0.015 |

TABLE 3

| Compound | Mole Percent (%) |
|---|---|
| $SiO_2$ | 65 |
| $Na_2O$ | 6.4 |
| $K_2O$ | 6.6 |
| $Al_2O_3$ | 4.1 |
| $TiO_2$ | 4.2 |
| $B_2O_3$ | 8.1 |
| ZnO | 5.6 |
| $Sb_2O_3$ | 0.2 |

Although the invention has been described in detail for the purpose of illustration, it is understood that such detail is solely for that purpose and variations can be made therein by those skilled in the art without departing from the spirit and scope of the invention which is defined by the following claims.

What is claimed is:

1. A substrate for supporting high-density biological and chemical arrays comprising:
   a boroaluminosilicate glass material having a sodium oxide content less of than 12 mole percent and a composition, in mole percent, consisting essentially of:

| | | | |
|---|---|---|---|
| $SiO_2$ | 64–70 | $Y_2O_3$ | 0–5 |
| $Al_2O_3$ | 9.5–14 | MgO | 0–5 |
| $B_2O_3$ | 5–10 | CaO | 3–13 |
| $TiO_2$ | 0–5 | SrO | 0–5.5 |
| $Ta_2O_5$ | 0–5 | BaO | 2–7 |
| $Nb_2O_5$ | 0–5 | MgO + CaO + SrO + BaO | 10–20 | and having a top surface with an average roughness of less than about 10 nanometers;
a uniform, functionalized coating of a polar silane covering at least a portion of a surface of said material; and
said substrate characterized in that the functionality of said coating is retained after immersion in boiling water for an amount of time exceeding 1 hour.

2. The substrate of claim 1, wherein said material has an average roughness of less than angstroms.

3. The substrate of claim 1, wherein said sodium oxide content is less than 8 mole percent.

4. The substrate of claim 1, wherein said polar silane contains an amine group.

5. The substrate of claim 1, wherein said polar silane contains at least one hydroxyl group.

6. The substrate of claim 1, wherein said polar silane contains at least one alkoxy group.

7. The substrate of claim 1, wherein said polar silane contains at least one chlorine group.

8. The substrate of claim 1, wherein said polar silane is aminopropyl triethoxysilane.

9. The substrate according to claim 1, wherein said substrate has a composition, in mole percent, consisting essentially of:

| | | | |
|---|---|---|---|
| $SiO_2$ | 67.6 | BaO | 4.31 |
| $Al_2O_3$ | 11.4 | MgO | 1.31 |
| $B_2O_3$ | 8.53 | SrO | 1.29 |
| CaO | 5.2 | $As_2O_3$ | 0.39 |

10. The substrate according to claim 1, wherein said substrate further comprises at least a binding entity selected from either a biological or chemical molecule, each having a specific affinity for another molecule through covalent or non-covalent bonding.

11. The substrate according to claim 1, wherein said binding entity includes: deoxyribonucleic acids (DNA), ribonucleic acids (RNA), synthetic oligonucleoides, antibodies, proteins, peptides, lectins, modified polysaccharides, synthetic composite macromolecules, functionalized nanostructures, synthetic polymers, modified/blocked nucleotides/nucelosides, modified/blocked amino acids, fluorophores, chromophores, ligands, chelates, and baptens.

12. A substrate for use in high density biological or chemical assays, said substrate comprising:
   a) a boroaluminosilicate glass with a composition having a sodium oxide content of less than about 12 mole percent;
   b) said substrate having a substantially flat, smooth surface with an average roughness of less than about 10 nanometers;
   c) a uniform, functionalized coating of a polar silane covering at least a portion of a surface of said substrate.

13. The substrate according to claim 12, wherein said substrate is characterized such that the functionality of said coating is retained after immersion in boiling water for an amount of time exceeding about 1 hour.

14. The substrate according to claim 12, wherein said substrate further comprises at least a binding entity selected from either a biological or chemical molecule, each having a specific affinity for another molecule through covalent or non-covalent bonding.

15. The substrate according to claim 14, wherein said binding entity includes: deoxyribonucleic acids (DNA), ribonucleic acids (RNA), synthetic oligonucleoides, antibodies, proteins, peptides, lectins, modified polysaccharides, synthetic composite macromolecules, functionalized nanostructures, synthetic polymers, modified/blocked nucleotides/nucelosides, modified/blocked amino acids, fluorophores, chromophores, ligands, chelates, and haptens.

16. The substrate of claim 12, wherein said surface has an average roughness of less than 5 angstroms.

17. The substrate of claim 12, wherein said polar silane contains an amine group.

18. The substrate of claim 12, wherein said polar silane contains at least one hydroxyl group.

19. The substrate of claim 12, wherein said polar silane contains at least one alkoxy group.

20. The substrate of claim 12, wherein said polar silane contains at least one chlorine group.

21. The substrate of claim 12, wherein said polar silane is aminopropyl triethoxysilane.

22. The substrate of clain 12, wherein said boroaluminosilicate glass has a composition, in terms of mole percent, consisting essentially of:

| | | | |
|---|---|---|---|
| $SiO_2$ | 64–70 | $Y_2O_3$ | 0–5 |
| $Al_2O_3$ | 9.5–14 | MgO | 0–5 |
| $B_2O_3$ | 5–10 | CaO | 3–13 |
| $TiO_2$ | 0–5 | SrO | 0–5.5 |
| $Ta_2O_5$ | 0–5 | BaO | 2–7 |
| $Nb_2O_5$ | 0–5 | MgO + CaO + SrO + BaO | 10–20 |

23. The substrate of claim 22, wherein said boroaluminosilicate glass has a composition, in mole percent, consisting essentially of:

| | | | |
|---|---|---|---|
| $SiO_2$ | 67.6 | BaO | 4.31 |
| $Al_2O_3$ | 11.4 | MgO | 1.31 |
| $B_2O_3$ | 8.53 | SrO | 1.29 |
| CaO | 5.2 | $As_2O_3$ | 0.39 |

* * * * *